United States Patent [19]

Seipp et al.

[11] Patent Number: 5,252,562

[45] Date of Patent: Oct. 12, 1993

[54] ACETOHYDROXAMIC COMPOUND AND COMPLEXES PHARMACEUTICAL COMPOSITIONS CONTAINING THEM AND PROCESSES OF PREPARATION AND USE

[75] Inventors: Ulrich Seipp, Aachen; Werner Englberger, Stolberg; Michael Haurand, Stolberg; Johannes Schneider, Stolberg, all of Fed. Rep. of Germany

[73] Assignee: Gruenenthal GmbH, Aachen, Fed. Rep. of Germany

[21] Appl. No.: 911,623

[22] Filed: Jul. 10, 1992

[30] Foreign Application Priority Data

Jul. 17, 1991 [DE] Fed. Rep. of Germany ....... 4123613

[51] Int. Cl.$^5$ .................... A61K 31/70; A61K 31/38; C07D 33/70
[52] U.S. Cl. ...................... 514/58; 514/438; 549/76; 536/103
[58] Field of Search .................... 549/76; 514/25, 438, 514/58; 536/103

[56] References Cited

U.S. PATENT DOCUMENTS

| | | | |
|---|---|---|---|
| 4,738,986 | 4/1988 | Kneen et al. | 514/575 |
| 4,977,188 | 12/1990 | Kneen et al. | 514/507 |
| 5,011,854 | 4/1991 | Takahashi et al. | 564/251 |
| 5,026,729 | 6/1991 | Brooks et al. | 562/621 |
| 5,036,157 | 7/1991 | Kneen et al. | 549/77 |

FOREIGN PATENT DOCUMENTS

| | | |
|---|---|---|
| 196184 | 10/1986 | European Pat. Off. . |
| 351214 | 1/1990 | European Pat. Off. . |
| 412939 | 2/1991 | European Pat. Off. . |
| 449722 | 10/1991 | European Pat. Off. . |
| WO 87/04152 | 7/1987 | PCT Int'l Appl. . |

OTHER PUBLICATIONS

R. Morrison et al., "Organic Chemistry" 3rd ed., pp. 639–641, Allyn and Bacon, Inc., Boston (1973).
Summers et al., "Orally Active Hydroxamic Acid Inhibitors of Leukotriene Biosynthesis", J. Med. Chem., 31, 3–5 (1988).
Tateson et al., in Brit. J. Pharmacol., 94, 528 to 539 (1988).
J. B. Summers et al., J. Med. Chem., 31, 1960 (1988).
H. Konzett et al. Naunyn Schniedeberg's Arch. Exp. Path. Pharma., vol. 195, 71 to 74 (1940).

Primary Examiner—Mark Russell
Attorney, Agent, or Firm—Evenson, McKeown, Edwards & Lenahan

[57] ABSTRACT

An acetohydroxamic acid compound of formula I

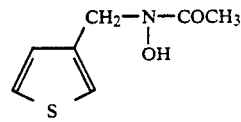

as such or in form of a complex with $\beta$-cyclodextrin or hydroxypropyl-$\beta$-cyclodextrin specifically inhibits 5-lipoxygenase and is useful in pharmaceutical compositions for prophylaxis and treatment of diseases due to the action of leucotrienes. The acetohydroxamic acid compound may be prepared by reacting 3-thiophenecarboxaldehyde with hydroxylamine or a salt thereof to form the corresponding oxime, reducing the oxime with a boron-containing reducing agent to form N-(thien-3-yl)methyl-hydroxylamine, and introducing an acetyl group.

13 Claims, No Drawings

ACETOHYDROXAMIC COMPOUND AND COMPLEXES PHARMACEUTICAL COMPOSITIONS CONTAINING THEM AND PROCESSES OF PREPARATION AND USE

BACKGROUND OF THE INVENTION

Polyunsaturated higher fatty acids such as arachidonic acid serve in the metabolism of mammals, including man, as substrates for the formation of physiologically important eicosanoids such as prostaglandins and leucotrienes (a group of compounds also known as "Slow Reacting Substance of Anaphylaxis" or "SRS-A"). The pathway to prostaglandins is catalyzed by cyclooxygenase (also named "prostaglandin synthetase") whereas the pathway to leucotrienes is catalyzed by 5 lipoxygenase. While prostaglandins show beneficial effects in mammals, leucotrienes or SRS A cause allergic reactions, bronchoconstrictions, inflammations, asthma and numerous other harmful effects.

Tateson et al. in Brit. J. Pharmacol. 94, 528 to 539 (1988) describe acetohydroxamic acid compounds which have a distinct inhibiting effect on 5 lipoxygenase but have only a weak inhibiting effect on cyclooxygenase. There remains a need, however, for chemically and metabolically stable agents which in the living organism have no effect on the biosynthesis of prostaglandins but inhibit selectively or specifically the activity of 5 lipoxygenase and thus prevent the formation of the undesired leucotrienes.

SUMMARY OF THE INVENTION

It is the object of the present invention to provide a new active agent which selectively or specifically inhibits the activity of 5-lipoxygenase.

It is also an object of the invention to provide a method for preparing pharmacologically useful acetohydroxamic acid compounds.

Another object of the invention is to provide new pharmaceutical compositions useful in the prophylaxis and/or treatment of leucotriene-mediated disorders, such as asthma, in mammals.

A further object of the invention is to provide methods of treating mammals, especially humans, subject to leucotriene-mediated disorders, such as asthma and the like.

These and other objects of the invention are achieved by providing an acetohydroxamic acid compound corresponding to the formula I

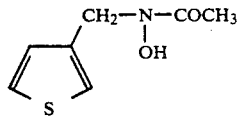

or a complex thereof with β-cyclodextrin or hydroxypropyl-β-cyclodextrin.

In accordance with another aspect of the invention, the objects are achieved by providing a process for preparing an acetohydroxamic acid compound corresponding to the formula I

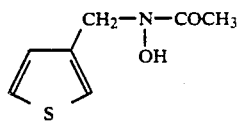

or a complex thereof with β-cyclodextrin or hydroxypropyl-β-cyclodextrin, comprising the steps of:

reacting 3-thiophenecarboxaldehyde with hydroxylamine or a salt thereof in the presence of a base to form the corresponding oxime, reducing the resulting oxime with a boron containing reducing agent in the presence of an acid to form N-(thien-3-yl)methyl-hydroxylamine;

acetylating the resulting hydroxylamine to form N-hydroxy-N-(thien-3-yl)methyl-acetamide; and if a cyclodextrin complex is to be formed, dissolving the resulting acetamide in an aqueous solution of a cyclodextrin selected from the group consisting of β-cyclodextrin and hydroxypropyl-β-cyclodextrin, and lyophilizing the resulting solution to form a complex of the N-hydroxy-N-(thien-3-yl)methyl-acetamide with the selected cyclodextrin.

In yet another aspect the objects of the invention are achieved by providing a pharmaceutical composition comprising an effective 5-lipoxygenase inhibiting amount of N-hydroxy-N-(thien-3-yl)methyl-acetamide and at least one pharmaceutical carrier or adjuvant.

In accordance with a still further aspect of the invention, the objects are achieved by providing a method for treating a mammal suffering from a leucotriene-mediated disorder comprising administering to the mammal an effective 5-lipoxygenase inhibiting amount of N-hydroxy-N-(thien-3-yl)methyl-acetamide.

DETAILED DESCRIPTION OF PREFERRED EMBODIMENTS

It has been found that the new acetohydroxamic acid compound of formula I

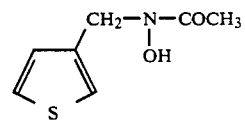

and its complexes with β-cyclodextrin or hydroxypropyl-β-cyclodextrin selectively inhibit the activity of 5 lipoxygenase when administered orally or parenterally. Because of this property, the acetohydroxamic acid compound and its complexes are suitable for prophylaxis and treatment of diseases for which is known that leucotrienes formed by the enzymatic action of 5 lipoxygenase act as mediators. Examples of such diseases include asthma, rheumatoid arthritis, psoriasis, allergic rhinitis, endotoxin shocks, anaphylactic shocks, ischemia induced myocardial injury as well as disorders of coronary and/or cerebral vessels.

Accordingly the present invention relates to the acetohydroxamic acid compound of formula I

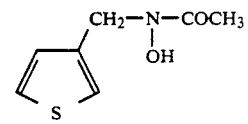

and its complexes with β-cyclodextrin or hydroxypropyl-β-cyclodextrin.

The invention further relates to a process for the preparation of the acetohydroxamic acid compound of formula I and its complexes with β-cyclodextrin or hydroxypropyl-β-cyclodextrin characterized in that 3 thiophenecarboxaldehyde is reacted with hydroxylamine or a salt thereof in the presence of a base to form the corresponding oxime which is reduced with a boron containing reducing agent in the presence of an acid to N-(thien-3-yl)methyl-hydroxylamine, into which the acetyl residue is introduced, and optionally the resulting acetohydroxamic acid compound of formula I is dissolved in an aqueous solution of β-cyclodextrin or hydroxypropyl-β-cyclodextrin and the resulting solution is lyophilized to form the corresponding complex.

The reaction of 3-thiophenecarboxaldehyde to the corresponding oxime is performed in a known manner, for instance in alcoholic or aqueous-alcoholic solution in the presence of a base, e.g. pyridine, potassium carbonate or sodium acetate, at temperatures of from 20° to 60° C.

The reduction of the oxime preferably is carried out using boron hydrides, especially sodium cyanoborohydride, in the presence of acetic acid or ethanolic hydrochloric acid at temperatures of from 20° to 60° C. or in an alcoholic solution with a borane-amine-complex, e.g. boranetrimethylamine-complex or borane-pyridine-complex, or with borane-tetrahydrofuran-complex in the presence of an acid, e.g. 6M hydrochloric acid at temperatures of from 0° to 50° C. (J. B. Summers et al., J. Med. Chem. 31, 1960 (1988)).

To prepare the desired acetohydroxamic acid compound N-hydroxy-N-(thien-3-yl)methyl-acetamide the N-(thien-3-yl)methyl-hydroxylamine, optionally without isolation from the reaction mixture in which it was prepared, is reacted with an acetylating agent, preferably acetic anhydride or acetyl chloride, in the presence of an agent capable of binding acids, e.g. pyridine or quinoline, whereby a compound of formula II

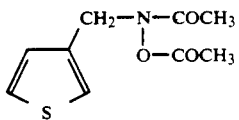

is formed. Upon treatment with a base in the presence of an alcoholic solvent, e.g. methanol or ethanol, at temperatures of about 20° to 60° C., the O-acetyl group is split off, and the desired compound of formula I is obtained. Suitable bases include potassium, sodium or lithium hydroxide, sodium or potassium carbonate or sodium hydrogen carbonate, which optionally may be added in form of an aqueous 0.1 to 1M solution to an alcoholic solution of the compound of formula II.

The complexes of the acetohydroxamic acid compound of formula I with B-cyclodextrin or hydroxypropyl-β-cyclodextrin are prepared by saturating aqueous, optionally sodium chloride containing, solutions of an aforementioned cyclodextrin with N hydroxy-N-(thien-3-yl)methyl-acetamide, filtering the resulting solution, and lyophilizing the filtrate. The resulting complexes show high solubility in water combined with excellent bioavailability of the active ingredient, N-hydroxy-N-(thien-3-yl)methyl-acetamide.

As already stated hereinabove, the acetohydroxamic acid compound of formula I has a specific inhibiting effect on 5 lipoxygenase which was determined, e.g. by in vitro experiments.

To determine the inhibition of 5 lipoxygenase, aliquots of freshly drawn, heparinized human blood were incubated at 37° C. in a water bath with addition of either N Hydroxy-N-(thien-3-yl)methyl-acetamide in different concentrations or a solvent. After 5 minutes the calcium ionophore A23187 was added to an end concentration of 15 μg/ml blood, and the incubation was continued for 30 minutes at 37° C. Then the samples were centrifuged to collect the cell free plasma. The content of the immunoreactive leucotriene $B_4$ ($iLTB_4$), in each sample was determined by radioimmunoassay "RIA" ($^3H$-$LTB_4$-RIA, Amersham) with reference to a $LTB_4$ standard curve and was calculated as ng $iLTB_4$/ml plasma. The percentage inhibition caused by the acetohydroxamic acid compound of formula I at various concentrations was calculated in comparison to the aliquots incubated with solvent only. N-hydroxy-N-(thien-3-yl)methyl-acetamide has an $IC_{50}$-value, i.e. the concentration causing an inhibition of 50% of 5 lipoxygenase, of 0.3 μmolar.

To determine the rate and the extent of the release of N hydroxy-N-(thien-3-yl)methyl-acetamide from the complex prepared according to Example 3, the 5 lipoxygenase activity of cell-free 5 lipoxygenase was polarographically measured with oxygen electrodes in 10,000 × g supernatant from homogenized rat basophilic leukemia cells (RBL i cells). After incubation of the 10,000 × g supernatant with arachidonic acid (75 μM), adenosine triphosphate (4 mM), glutathione (4 mM), and either N hydroxy-N-(thien-3-yl)methyl-acetamide or a solvent for 5 minutes at 35° C., the lipoxygenase reaction was initiated by addition of calcium chloride and plotted simultaneously. The evaluation included the duration of the lag-phase as well as the initial rate of the reaction after the lag-phase. The complex prepared according to Example 3 and N-hydroxy-N-(thien-3-yl)methyl-acetamide as such caused comparable effects with respect to the prolongation of the lag-phase and the inhibition of the 5 lipoxygenase reaction. Furthermore, tests with different incubation periods showed that the acetohydroxamic acid compound was released from the complex without any substantial time-lag. A significant amount of the acetohydroxamic acid compound is fully available in the biological test system even when the compound is originally administered in the form of a complex.

The effect of the acetohydroxamic acid compound of formula I on the activity of cyclooxygenase was tested using a suspension of sheep seminal vesicle microsomes in 50 μM of potassium phosphate buffer of pH 7.0 which was incubated either with N-hydroxy-N-(thien-3-yl)methyl-acetamide or with a solvent only and [$^{14}C$]-arachidonic acid. The $IC_{50}$ values, i.e. the concentrations causing an inhibition of 50% of cyclooxygenase were determined by thin layer chromatography using a TLC-linear-analyzer. It has been found that the $IC_{50}$-values for the inhibition of cyclooxygenase were significantly higher than the $IC_{50}$-values for the inhibition of 5-lipoxygenase, i.e. the acetohydroxamic acid compound of formula I inhibits very specifically the activity of 5-lipoxygenase.

The aforementioned favorable activity profile of the acetohydroxamic acid compound of formula I could not have been predicted based on the known state of the prior art. European patent application No. EP 351,214 discloses an acetohydroxamic acid compound which exhibits an inhibiting effect on lipoxygenase as well as on cyclooxygenase. European patent application No. EP 196,184 refers to acylhydroxamic acid derivatives having lipoxygenase and/or cyclooxygenase inhibitory properties, especially cyclooxygenase inhibitory properties (page 9, column 13, lines 26 to 29). Thus, it was not possible to predict whether and against which enzyme the acetohydroxamic acid compound of formula I would show a largely selective inhibiting effect.

The bioavailability of the compound of formula I was characterized by means of an ex vivo biochemical assessment method described by Tateson et al. in Brit. J. Pharmacol. 528 (1988): N-Hydroxy-N-(thien-3-yl)methyl-acetamide was orally administered in a dose of 21.5 mg/kg to male rats (Wistar strain). One hour later blood was taken from the rats in lethal $CO_2$-narcosis. Aliquots of the blood were incubated for 30 minutes at 37° C. in a water bath with addition of calcium ionophore A 23 187 to an end concentration of 15 μg/ml. At the end of the incubation the samples were centrifuged to collect the cell free plasma. The concentration of the immunoreactive $LTB_4$(i$LTB_4$ ng/ml) in each plasma sample was determined by radioimmunoassay ($^3$H-$LTB_4$-RIA, Amersham) by means of a $LTB_4$-standard curve in diluted rat plasma. To determine the percent inhibition of ex vivo i$LTB_4$-formation in whole blood of rats treated with the compound of formula I, rats orally treated with an appropriate vehicle solution were included in all experiments, aliquots of their blood were run in parallel and were processed in the same manner as described. The mean i$LTB_4$formation per ml plasma of these vehicle treated rats served as the 100% value of normal 5-lipoxygenase activity. The percent inhibition of the ex vivo i$LTB_4$-formation after oral administration of the compound of formula I was calculated according to the following formula:

$$\% \text{ inhibition} = 100 - (100 \times Q/C)$$

where Q represents the mean i$LTB_4$ content in ng i$LTE_4$ per ml plasma of the rats treated with the compound of formula I and C represents the mean i$LTB_4$ content in ng i$LTB_4$ per ml plasma of rats treated only with the vehicle. The acetohydroxamic acid compound of formula I showed an inhibition of 95%, i.e. an excellent oral availability (the calculated dose with a semimaximum inhibiting effect after oral administration was 5.6 mg/kg).

The antiasthmatic effect of the compound according to the invention was tested in anesthetized and ventilated guinea pigs. In order to induce an asthmatic reaction, the animals were passively sensitized with a single intraperitoneal injection of antiovalbumin serum. After 48 hours the asthmatic reaction was elicited by intravenous challenge with 0.2 mg/kg of ovalbumin. The immediately resulting bronchoconstriction was measured as an increase in overflow according to the Konzett-Roessler method for a period of 10 minutes (Naunyn Schiedeberg's Arch. Exp. Path. Pharma. Vol. 195, 71–74 (1940)). Effects caused by histamine, serotonin and sympathic counterreaction were eliminated by intravenous pretreatment with 2.15 mg/kg of mepyramine, 46.4 mg/kg of propranolol, 4.64 mg/kg of atropine and 1 mg/kg of methysergide, all given 5 minutes before challenge. N-Hydroxy-N-(thien-3-yl)methyl-acetamide was orally administered 60 minutes before, intravenously administered 30 minutes before, and locally administered 2 minutes before the administration of ovalbumin.

The following table shows the inhibition of the bronchoconstriction after administration of N-hydroxy-N-(thien-3-yl)methyl-acetamide in comparison with a control group treated only with a vehicle solution.

| acetohydroxamic acid compound of Example No. | dose [mg/kg] | manner of administration | inhibition of bronchoconstriction |
|---|---|---|---|
| 1 | 21.5 | oral | 42% |
| 3 | 21.5* | intravenous | 49% |
| 3 | 10.0* | local | 56% |

*based on the complexed N-hydroxy-N-(thien-3-yl)methyl-acetamide content

The results show surprisingly that the complex prepared according to example 3 has a stronger inhibiting effect after local administration with half of the dose than after intravenous administration. The finding that the effects of N-hydroxy-N-(thien-3-yl)methyl-acetamide as such after oral administration of 21.5 mg/kg were equal to the effects of N-hydroxy-N-(thien-3-yl)methyl-acetamide in the form of a complex after intravenous administration of 21.5 mg/kg indicate a high resorption of the acetohydroxamic acid compound.

The anti-anaphylactic effect of N-hydroxy-N-(thien-3-yl)methyl-acetamide was tested using an in vitro model. Isolated, spirally cut tracheal strips of guinea pigs actively sensitized by intraperitoneal administration of 10 μg of ovalbumin together with 20 mg of aluminum hydroxide as adjuvant three weeks before testing were added to organ baths which had a temperature of 37° C. and contained a nutrient solution saturated with carbogen (a mixture of 95% oxygen and 5% carbon dioxide). The organs were connected to isometric force transducers. After incubation with mepyramine (elimination of histamine) and indomethacin (inhibition of cyclooxygenase resulting in an increase of the anaphylactic reaction) ovalbumin was added to the organ bath in cumulatively increasing concentrations. The resulting anaphylactic constrictions were inhibited by N-hydroxy-N-(thien-3-yl)methyl-acetamide which was added to the organ bath before the anaphylactic constrictions were elicited. The $IC_{50}$-values, i.e. the concentrations causing an inhibition of 50% of the anaphylactic constrictions in the isolated tracheal strips of guinea pigs are given in the following table:

| acetohydroxamic acid compound of Example No. | $IC_{50}$-value [μmolar] |
|---|---|
| 1 | 10.2 |
| 3* | 18.7 |

*based on the complexed N-hydroxy-N-(thien-3-yl)methyl-acetamide content

Due to their favorable effects on the metabolism of polyunsaturated fatty acids, particularly their selective inhibitory action on the 5-lipoxygenase induced production of metabolites of arachidonic acid such as 5-hydroperoxy eicosatetraenoic acid (5-HPETE), 5-hydroxyeicosatetraenoic acid (5-HETE) or SRS-A, respectively, the acetohydroxamic acid compound of formula I exhibits various physiologically valuable activities such as anti-anaphylactic, anti-asthmatic, anti-allergic, anti-phlogistic, blood pressure lowering and cerebral- and coronary-circulation improving effects, decreasing the risk of leucocyte aggregation and preventing the formation of leucocyte thrombi. Due to their chemical stability, and to their metabolic stability when used as therapeutic agents, N-hydroxy-N-(thien-3-yl)methylacetamide is storable and suitable for use as a medicament such as an anti-anaphylactic, an anti-asthmatic, an anti-allergic, an anti-phlogistic, an anti-hypertensive agent, an anti-thrombotic agent, an agent for use in treatment or prophylaxis of ischemic myocardial infarction, disorders of coronary and/or cerebral vessels, or an agent which combats Morbus Crohn.

N-Hydroxy-N-(thien-3-yl)methyl-acetamide has a low degree of toxicity which is observed only at far higher doses than those to be administered for therapeutic or prophylactic purposes. Accordingly this compound can be administered to humans and animals.

The invention also relates to medicaments containing as active ingredient the acetohydroxamic acid compound of formula I, optionally in form of a complex with β-cyclodextrin or hydroxypropyl-β-cyclodextrin. The dosage of this active ingredient to be administered depends, for instance, on the body weight, on the route and form of administration, on the indication, and on the state of disease in the individual to be treated. Taking these factors into account, a unit dosage form of a medicament according to the present invention generally will contain from about 0.01 to about 1000 mg of the active ingredient, whereby compositions for parenteral, oral or rectal administration contain about 0.01 to about 1000 mg, and compositions for topical or inhalative administration contain about 0.01 to about 100 mg, per unit dose.

Medicaments for parenteral administration may be solutions or suspensions, but may also be dry formulations suitable for easy reconstitution.

Spray forms are very useful application forms for intranasal or oral administration of the compound of formula I or for the administration of this substance to the bronchia.

Orally administrable compositions such as tablets, dragees, capsules, granules, drops and syrups are very suitable for prophylactic or therapeutic administration of the acetohydroxamic acid compound of formula I in many situations, optionally in form of a complex with β-cyclodextrin or hydroxypropyl-β-cyclodextrin. Other compositions such as suppositories or compositions for percutaneous administration of the compound of formula I, such as plasters or the like containing a solution of the active ingredient and optionally a known membrane penetration enhancer (such as a N-alkyl lactam) are often also very convenient. The pharmaceutical compositions described above for oral, rectal, or percutaneous administration of the compound of formula I preferably may be such from which at least a portion of the active ingredient has a delayed release. Thus, a steady supply of the active ingredient to the individual can be achieved for a longer period of time, for instance 24 hours.

All of the general types of pharmaceutical compositions to which the invention is applicable as well as the preparation of these compositions are known per se and since N-hydroxy-N-(thien-3-yl)methyl-acetamide is chemically stable the incorporation into pharmaceutical compositions in the form and dosage desired poses no problems for an ordinarily skilled pharmacist. In the production of pharmaceutical compositions according to the invention conventionally used inorganic or organic adjuvants such as carriers, diluents, solvents, binders, lubricants, tablet disintegrating agents, colors, flavorings are formulated together with the active ingredient of formula I in accordance with accepted standards in a known manner. Compositions for parenteral use must be sterile and, if prepared in liquid form, isotonic.

EXAMPLES

All temperature references are uncorrected. The 1H-nuclear magnetic spectra (1H-NMR) were measured at 300 MHz. The chemical shifts are given in ppm.

In column chromatography, silica gel ("Kieselgel 60", 0.040 to 0.063 mm from E. Merck, Darmstadt, Germany) was used as the stationary phase. The reactions were monitored by thin layer chromatography on plates precoated with silica gel ("HPTLC Fertigplatten, Kieselgel 60 F 254" from E. Merck, Darmstadt, Germany). The ratio of the components of the solvent mixtures used in all of the chromatographic procedures is given in volume/volume.

EXAMPLE 1

Preparation of
N-hydroxy-N-(thien-3-yl)methyl-acetamide a) 3-thiophenecarboxaldehyde oxime (syn/anti-mixture)

11.2 g of 3-thiophenecarboxaldehyde, 7 g of hydroxylamine hydrochloride and 5.5 g of sodium carbonate were stirred in 200 ml of ethanol/water (1:1) at room temperature for 17 hours. Then the reaction mixture was poured into 500 ml of an aqueous saturated solution of sodium chloride and extracted three times with 250 ml portions of ethyl acetate. The combined organic layers were washed with an aqueous saturated solution of sodium chloride, dried over magnesium sulfate, filtered and evaporated under vacuum at 40° C. to yield 14.19 g of 3-thiophenecarboxaldehyde oxime.

b) N-(thien-3-yl)methyl-hydroxylamine

To 11.45 g of the oxime prepared according to Example 1a) in 450 ml of glacial acetic acid were added 9 g of sodium cyanoborohydride at room temperature. The mixture was stirred at room temperature for 2 hours.

c) N-acetoxy-N-(thien-3-yl)methyl-acetamide

To the solution containing N-(thien-3-yl)methyl-hydroxylamine prepared according to example 1b) were added 70.9 ml of acetic anhydride at room temperature. After stirring for 17 hours, the mixture was evaporated at 60° C. under vacuum. 150 ml of ethyl acetate were added to the resulting residue, and the mixture was poured into 700 ml of water. Then sodium hydrogen carbonate was added to the mixture until carbon dioxide was no longer formed. The organic layer was separated, and the aqueous layer was washed with ethyl acetate. Then the combined organic layers were dried over magnesium sulfate and evaporated under vacuum at 40° C. Chromatographic purification with hexane/isopropanol/glacial acetic acid (4.5:0.5:0.05) yielded 13.27 g of N-acetoxy-N-(thien-3-yl)methyl-acetamide in the form of a pale yellow oil.

d) N-hydroxy-N-(thien-3-yl)methyl-acetamide

To a solution of 3.68 g of the bisacetyl compound prepared according to Example 1c) in 56 ml of methanol were added 22.5 ml of a 1 molar solution of lithium hydroxide in methanol at room temperature. After stirring for 45 minutes the reaction mixture was added to 150 ml of an aqueous saturated solution of sodium chloride and 40 ml of an aqueous saturated solution of sodium hydrogen carbonate and extracted with ethyl acetate. The combined organic layers were washed with an aqueous saturated solution of sodium chloride, dried over magnesium sulfate, filtered and evaporated under vacuum at 40° C. After chromatographic purification with hexane/ethyl acetate/methanol (4:6:0.5) and recrystallization from ethyl acetate, 1.8 g of N-hydroxy-N-(thien-3-yl)methyl-acetamide were obtained in the form of a colorless solid melting at 92° C. to 93° C.

$^1$H-NMR (DMSO-d$_6$): 2.03 (s, 3H); 4.66 (s, 2H); 7.03 (m, 1H); 7.31 (d, 2Hz, 1H); 7.43 (m, 1H); 9.87 (s, 1H).

EXAMPLE 2

Preparation of a complex with β-cyclodextrin

To a solution of 1.8 g of β-cyclodextrin in 100 ml of water were added 1.36 g of N-hydroxy-N-(thien-3-yl)methyl-acetamide at room temperature. After stirring for 17 hours the mixture was filtered, and the resulting filtrate was lyophilized to yield 3.1 g of a colorless powder containing 44% by weight of N-hydroxy-N-(thien-3-yl)methyl-acetamide. The acetamide content was determined by comparing the UV-extinctions of standard solutions of the complex with the UV-extinctions of N-hydroxy-N-(thien-3-yl)methylacetamide.

EXAMPLE 3

Preparation of a complex with hydroxypropyl-β-cyclodextrin

Following the procedure described in Example 2, 0.86 g of N-hydroxy-N-(thien-3-yl)methyl-acetamide were added to a solution of 5 g of hydroxypropyl-β-cyclodextrin in 10 ml of an aqueous solution containing 0.9% by weight of sodium chloride to yield 5.3 g of a colorless powder containing 14.3% by weight N-hydroxy-N-(thien-3-yl)methyl-acetamide. The acetamide content was determined as in Example 2.

The complexes obtained according to Examples 2 and 3 have high solubilities in water which in turn result in their good bioavailability mentioned above. Since hydroxypropyl-β-cyclodextrin has especially good compatibility, the use of complexes of N-hydroxy-N-(thien-3-yl)methyl-acetamide is particularly advantageous for certain application forms, e.g. liquid preparations for oral or parenteral administration or dry formulations which readily dissolve.

Some solubility data is given in the following table:

| Solvent | Solubility in mg/ml Compound of | | |
|---|---|---|---|
| | Example 1 | Example 2 | Example 3 |
| phosphate buffer (pH 7.4)/ ethanol, 4:1 mixture | 3 | | |
| phosphate buffer (pH 7.4) | | 53 (22)* | 560 (82)* |
| water/ethanol 4:1 mixture | 3 | | |
| water | | 56 (23)* | 360 (53)* |

*Corresponding amount of pure N-hydroxy-N-(thien-3-yl)methyl-acetamide

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An acetohydroxamic acid compound corresponding to the formula I

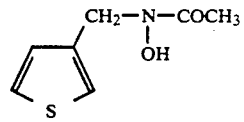

or a complex thereof with β-cyclodextrin or hydroxypropyl-β-cyclodextrin.

2. A pharmaceutical composition comprising an effective 5-lipoxygenase inhibiting amount of N-hydroxy-N-(thien-3-yl)methyl-acetamide and at least one pharmaceutical carrier or adjuvant.

3. A pharmaceutical composition according to claim 2, wherein said N-hydroxy-N-(thien-3-yl)methyl-acetamide is in the form of a complex with a cyclodextrin selected from the group consisting of β-cyclodextrin and hydroxypropyl-β-cyclodextrin.

4. A pharmaceutical composition according to claim 2, containing from 0.01 to 1000 mg of said N-hydroxy-N-(thien-3-yl)methyl-acetamide per unit dose.

5. A parenterally administrable pharmaceutical composition according to claim 2, comprising a sterile, isotonic, parenterally acceptable liquid vehicle containing per unit dose from 0.1 to 1000 mg of said N-hydroxy-N-(thien-3-yl)methyl-acetamide.

6. An orally administrable pharmaceutical composition according to claim 2, comprising a tablet, dragee or capsule containing per unit dose from 0.1 to 1000 mg of said N-hydroxy-N-(thien-3-yl)methyl-acetamide and at least one pharmacologically acceptable carrier or adjuvant.

7. An orally administrable pharmaceutical composition according to claim 6, wherein at least part of said N-hydroxy-N-(thien-3-yl)methyl-acetamide is in delayed release form.

8. An intranasally administrable pharmaceutical composition according to claim 2, comprising an effective 5-lipoxygenase inhibiting amount of said N-hydroxy-N-(thien-3-yl)methyl-acetamide in a sprayable, pharmaceutically acceptable carrier.

9. A pharmaceutical composition according to claim 2, which comprises an adjuvant selected from the group consisting of pharmaceutically acceptable binders, lubricants and tablet disintegrating agents.

10. A method for treating a mammal suffering from a leucotriene-mediated disorder comprising administering to said mammal an effective 5-lipoxygenase inhibiting amount of N-hydroxy-N-(thien-3-yl)methyl-acetamide.

11. A method according to claim 10, wherein said N-hydroxy-N-(thien-3-yl)methyl-acetamide is in the form of a complex with a cyclodextrin selected from the group consisting of β-cyclodextrin and hydroxypropyl-β-cyclodextrin.

12. A method for treating a patient suffering from asthma, comprising administering to said patient an effective asthma alleviating amount of N-hydroxy-N-(thien-3-yl)methyl-acetamide.

13. A method according to claim 12, wherein said N-hydroxy-N-(thien-3-yl)methyl-acetamide is in the form of a complex with a cyclodextrin selected from the group consisting of β-cyclodextrin and hydroxypropyl-β-cyclodextrin.

* * * * *